US009918943B2

(12) United States Patent
Barua

(10) Patent No.: US 9,918,943 B2
(45) Date of Patent: Mar. 20, 2018

(54) SYSTEMS AND METHODS FOR ENDOTOXIN REMOVAL FROM FLUIDS

(71) Applicant: Sutapa Barua, Rolla, MO (US)

(72) Inventor: Sutapa Barua, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 204 days.

(21) Appl. No.: 15/130,564

(22) Filed: Apr. 15, 2016

(65) Prior Publication Data

US 2016/0304361 A1    Oct. 20, 2016

Related U.S. Application Data

(60) Provisional application No. 62/178,647, filed on Apr. 15, 2015.

(51) Int. Cl.
*A61K 9/51* (2006.01)
*A61K 31/4745* (2006.01)
*A61K 47/48* (2006.01)
*G01N 33/50* (2006.01)

(52) U.S. Cl.
CPC .......... *A61K 9/5153* (2013.01); *A61K 9/5192* (2013.01); *A61K 31/4745* (2013.01); *A61K 47/48584* (2013.01); *A61K 47/48907* (2013.01); *G01N 33/50* (2013.01)

(58) Field of Classification Search
None
See application file for complete search history.

(56) References Cited

U.S. PATENT DOCUMENTS

2007/0053845 A1   3/2007  Sengupta et al.
2014/0212335 A1*  7/2014  Lee ..................... A61L 2/00
                                                        422/30
2014/0363514 A1   12/2014 Koyakutty et al.

FOREIGN PATENT DOCUMENTS

WO        2013124867 A1    8/2013

OTHER PUBLICATIONS

Non-Final Office Action dated Jul. 10, 2017 in U.S. Appl. No. 15/130,544, 10 pages.

* cited by examiner

*Primary Examiner* — Chester T Barry
(74) *Attorney, Agent, or Firm* — Shook, Hardy & Bacon L.L.P.

(57) ABSTRACT

Systems and methods are provided for the removal of endotoxins from fluids. The methods can include the use of polymeric nanoparticles for binding endotoxins present in a fluid. The polymeric nanoparticles can be associated with a support member. The polymeric nanoparticles can have an endotoxin removal capacity of at least $1\times10^9$ endotoxin units per gram of polymeric nanoparticle (EU/g) and/or a removal efficacy per unit surface area of the polymeric nanoparticles of at least $1\times10^6$ EU/cm$^2$.

20 Claims, 14 Drawing Sheets

SYSTEMS AND METHODS FOR ENDOTOXIN REMOVAL FROM FLUIDS

CROSS-REFERENCE TO RELATED APPLICATIONS

This application claims priority to U.S. Provisional Application Ser. No. 62/178,647 entitled "POLYMERIC NANOPARTICLES FOR DRUG DELIVERY AND BACTERIAL TOXIN REMOVAL," filed Apr. 15, 2015, the disclosure of which is hereby incorporated by reference as if set forth in its entirety herein.

FIELD

Systems and methods are provided for the removal of endotoxins from fluids.

BACKGROUND

Antigenic responses to gram-negative bacterial infections, gram-positive bacterial infections, fungal infections, and/or parasite infections in human beings can be stimulated by endotoxins released from bacterial or other cell membranes when the cell membranes are ruptured through processes such as enzymatic reactions. The release of such endotoxins may trigger sepsis or septic shock in patients, which can lead to organ failure and/or death.

SUMMARY

In one aspect, an endotoxin removal system is provided. The endotoxin removal system includes a plurality of polymeric nanoparticles. Each polymeric nanoparticle of the plurality of polymeric nanoparticles has a maximum dimension between 300 nm and 500 nm. The endotoxin removal system also includes a support member associated with the plurality of polymeric nanoparticles, where, when an aqueous solution including endotoxin molecules is exposed to the endotoxin removal system, the support member and the plurality of polymeric nanoparticles are cooperatively configured to separate at least a portion of the endotoxin molecules from the aqueous solution. Each polymeric nanoparticle of the plurality of polymeric nanoparticles has an endotoxin removal capacity of at least $1 \times 10^9$ endotoxin units per gram of polymeric nanoparticle (EU/g).

In another aspect, a method for removing endotoxins from an aqueous solution is provided. The method includes exposing an aqueous solution including endotoxin molecules to polymeric nanoparticles so that at least a portion of the endotoxin molecules bind to an exterior surface of one or more of the polymeric nanoparticles to form endotoxin-bound polymeric nanoparticles. Each of the polymeric nanoparticles has a maximum dimension of about 300 nm to about 500 nm. Each of the polymeric nanoparticles have an endotoxin removal capacity of at least $1 \times 10^9$ endotoxin units per gram of polymeric nanoparticle (EU/g). The method also includes removing at least a portion of the aqueous solution from the endotoxin-bound polymeric nanoparticles.

In yet another aspect, a method for removing endotoxins from an aqueous solution is provided. The method includes exposing an aqueous solution including endotoxin molecules to polymeric nanoparticles so that at least a portion of the endotoxin molecules bind to an outer surface of one or more of the polymeric nanoparticles to form endotoxin-bound polymeric nanoparticles, where at least the outer surface of each of the polymeric nanoparticles includes Poly(ε-caprolactone) (PCL). Each of the polymeric nanoparticles has a maximum dimension of about 300 nm to about 500 nm, and the polymeric nanoparticles have an endotoxin removal capacity of at least about $1 \times 10^9$ endotoxin units per gram of polymeric nanoparticle (EU/g) and an endotoxin removal efficacy of at least $1 \times 10^6$ endotoxin units per $cm^2$ of nanoparticle surface area (EU/$cm^2$).

BRIEF DESCRIPTION OF THE SEVERAL VIEWS OF THE DRAWINGS

The present invention is described in detail below with reference to the attached drawing figures, wherein.

DETAILED DESCRIPTION

Figure 1:
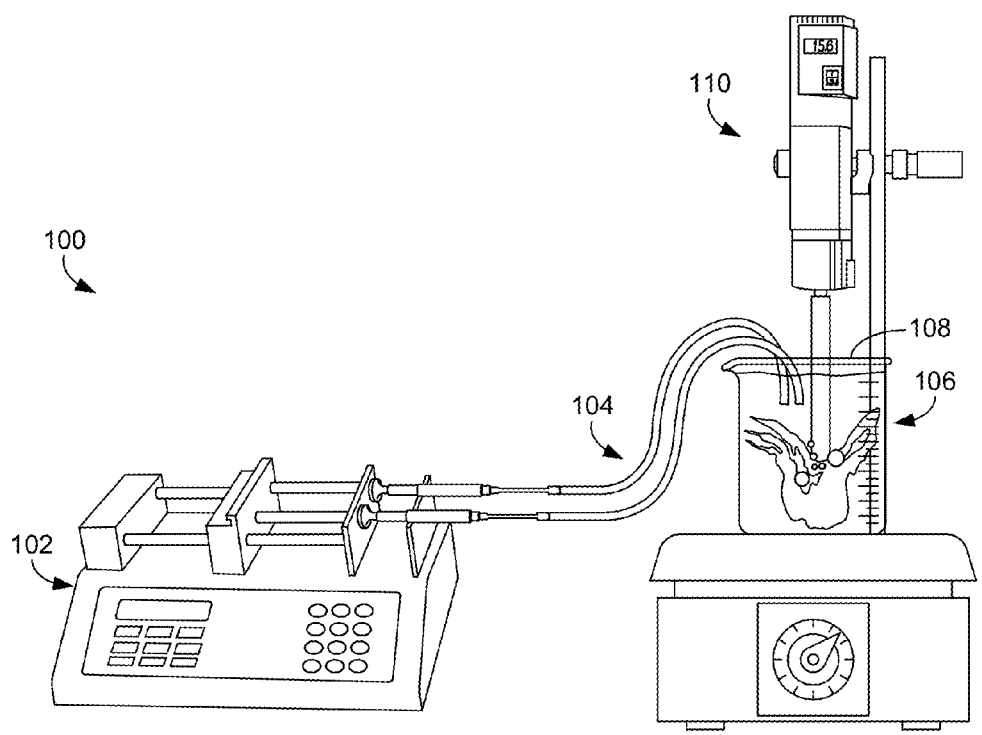
FIG. 1 is a schematic depiction of an exemplary phase separation system for making polymeric nanoparticles, according to an aspect of the invention.

In various aspects, an endotoxin removal system and methods for removing endotoxins from various fluids are disclosed. In certain aspects, the endotoxin removal system can include polymeric nanoparticles capable of binding to endotoxins present in an aqueous solution. In one or more aspects, the polymeric nanoparticles can be associated with a support member, such as a film or beads, which can be used together to filter an aqueous solution and remove endotoxin present in the solution.

The control of microbial infections is important for the preparation of biological media including water, in order to prevent or reduce the number of deaths claimed by septic shock or sepsis. This is particularly important because sepsis is one of the leading causes of death around the world with an incidence estimated to be 18 million cases per year with 0.75 million cases in the U.S. alone, with this number being higher in areas where clean water sources are not readily available. Additionally, sepsis is a common occurrence in clinical and hospital settings and more than half a million patients are affected every year. Sepsis can be caused by both Gram-positive and Gram-negative bacteria and some of the more common organisms responsible include, for example: *Escherichia coli* (*E. coli*), *Pseudomonas aeruginosa*, *Chlamidya*, *Staphyloccocus*, *Listeria*, and *Streptococcus*. The bacterial cell membranes of these microorganisms can release negatively or positively charged endotoxins, respectively, depending on whether they are Gram-negative or Gram-positive bacteria, when damaged. When the bacterial cell membranes are damaged by, for example, enzymatic reactions, the endotoxins released, may cause a host of antigenic and inflammatory responses, in for example, a human body.

One way to prevent bacterial infections is by removing the bacteria from the different sources, such as water. Various methods including distillation, ethylene oxide treatment, filtration, and irradiation have been employed to remove endotoxins from contaminated fluids, some methods being more efficient than others. These methods are mainly based on adsorption, filtration, ionic interactions, and phase separation techniques. However, these methods have poor selectivity and a low endotoxin binding ability, therefore, the overall efficiency of endotoxin removal of these methods remains low. In other words, these methods are not efficient in decreasing the endotoxin levels in a fluid to lower than 0.05 ng/ml (0.5 endotoxin units/ml), which is the safest exposure level to endotoxins, as determined by the U.S. Food and Drug Administration.

Polylysine immobilized cellulose porous microspheres have been used to remove endotoxins from protein solutions. In this method, proteins elute quickly due to their large size, while endotoxins diffuse into the particle pores and are retained inside the microspheres. However, the adsorption kinetics of these microspheres is slow making it a time consuming process to achieve a safe endotoxin concentration level of 0.05 ng/ml. Additionally, these microspheres are highly polydisperse, making it difficult to have a predictable efficiency when used repetitively. Other endotoxin removal methods suffer from a low elute volume, poor selectivity, poor efficiency, filtration fouling, and/or are economically unviable.

The endotoxin removal system and methods disclosed herein solve one or more of the above problems. The methods and systems described herein have shown to be much more efficient than the known methods for endotoxin removal. For example, the methods and systems disclosed herein include the synthesis and use of polymeric nanoparticles to efficiently sequester and/or bind endotoxins from contaminated fluids. In certain aspects, the polymeric nanoparticles can have an endotoxin removal capacity of at least about $1 \times 10^9$ endotoxin units per gram of polymeric nanoparticle (EU/g), which is several orders of magnitude higher than that of current commercially available endotoxin removal systems, such a porous silica gel matrix. As used herein, endotoxin units (EU) refers to 0.1 to 0.2 nanograms of endotoxin per mL. In the same or alternative aspects, the polymeric nanoparticles can exhibit an endotoxin removal efficacy of at least $1 \times 10^6$ EU per unit surface area ($cm^2$) of the polymeric nanoparticles, which is about an order of magnitude higher than commercially available hydrophobic charged microporous membranes.

In one or more aspects, the polymeric nanoparticles disclosed herein can bind to endotoxins from various types of bacteria, such as Gram-negative and/or Gram-positive bacteria. In one aspect, the polymeric nanoparticles can bind to an endotoxin from one or more Gram-negative bacterial species. In such aspects, the one or more Gram-negative bacterial species includes *E. coli*.

In various aspects, the polymeric nanoparticles can include one or more polymers. In certain aspects, the polymer can be any polymer that includes an aliphatic region or moiety that can hydrophobically interact with one or more endotoxins to bind the endotoxin(s) to the polymeric nanoparticle. In the same or alternative aspects, the polymer can be a polymer that includes an ionic region or moiety that can electrostatically interact with one or more endotoxins to bind the endotoxin(s) to the polymeric nanoparticle. In one aspect, the polymer can include both ionic and aliphatic regions that are configured to interact with one or more endotoxins via electrostatic interactions and via hydrophobic interactions to bind the endotoxin(s) to the polymeric nanoparticle.

A non-limiting list of exemplary polymers that can be included in the polymeric nanoparticles includes polyesters, such as Poly(ϵ-caprolactone) (PCL), polylactic acid (PLA), Poly(lactic-co-glycolic acid (PLGA), hyaluronic acid (HA), poly(acrylic acid) (PAA), poloxamers, polyethylene oxide (PEO), polyethylene glycol (PEG), and polyflutamic acid. In certain aspects, the polymer can be biodegradable. By using a biodegradable or a biocompatible polymer, environmental benefits can be provided in addition to a significant reduction of undesired bacterial toxicity, via endotoxin removal from a fluid. Such considerations are of great importance for both water purification and treatment of other types of biological media or components that suffer from microbial contaminations.

In certain aspects, when the polymeric nanoparticles comprises a polyester, the polyester can be characterized as an aliphatic polyester. An aliphatic polyester as used herein refers to a polyester having an aliphatic region that is capable of engaging in hydrophobic interactions with another molecule, such as an endotoxin.

In one or more aspects, the polymeric nanoparticles can comprise, consist essentially of, or consist of one or more biodegradable polymers. In certain aspects, the polymeric nanoparticles can comprise, consist essentially of, or consist of one or more polyesters. In one aspect, the polymeric nanoparticles can comprise, consist essentially of, or consist of PCL.

In various aspects, the outer surface of the polymeric nanoparticles can comprise, consist essentially of, or consist of: one or more biodegradable polymers. In certain aspects, the outer surface of the polymeric nanoparticles can comprise, consist essentially of, or consist of one or more polyesters. In one aspect, the outer surface of the polymeric nanoparticles can comprise, consist essentially of, or consist of PCL.

In certain aspects, the polymeric nanoparticles can have a maximum dimension of at least about 200 nm, at least about 250 nm, or at least about 300 nm; about 700 nm or less, about 600 nm or less, or about 500 nm or less; or about 200 nm to about 700 nm, about 200 nm to about 600 nm, about 200 nm to about 500 nm, about 250 nm to about 700 nm, about 250 nm to about 600 nm, about 250 nm to about 500 nm, about 300 nm to about 700 nm, about 300 nm to about 600 nm, or about 300 nm to about 500 nm. As used herein, maximum dimension refers to the maximum dimension of a nanoparticle, which can include a maximum diameter, maximum length, maximum width, or maximum depth. For example, for a spherical polymeric nanoparticle, the maximum dimension would refer to the maximum diameter. In another example, for a rod-shaped polymeric nanoparticle, the maximum dimension refers the largest of the length, width, and depth of the rod-shaped nanoparticle.

In certain aspects, the polymeric nanoparticles can have a substantially uniform size. In alternative aspects, the polymeric nanoparticles can have different sizes. In various aspects, the polymeric nanoparticles can have a polydispersity index value of about 0.05, 0.1, 0.2, 0.3, or 0.4.

In various aspects, the polymeric nanoparticles can be any shape or mixture of shapes. A non-limiting list of nanoparticle shapes includes sphere-shaped, rod-shaped, and disk-shaped. In certain aspects, the polymeric nanoparticles can be substantially one shape, such as approximately spherical.

In one or more aspects, the polymeric nanoparticles can remove at least about 60% of an endotoxin present in an endotoxin-containing aqueous solution, at least about 65%, at least about 70%, or at least about 75%. The % endotoxin removal can be determined using any conventional molecular techniques known to one skilled in the art. An exemplary method for measuring the % endotoxin removal can include the use of a fluorescent displacement assay, such as a BODIPY-Cadaverine (BC)-based fluorescence assay using $E.\ coli$ 055:B5 endotoxin. As used herein BODIPY refers to boron-dipyrromethene and is a commercially available fluorescence dye, for example, available at Sigma. In this assay, the fluorescence intensity may be measured for given concentrations of BC and the 055:B5 endotoxin, or other endotoxins, in a particular sample prior to endotoxin removal and after endotoxin removal from the particular sample. As endotoxins became bound to the surfaces of the polymeric nanoparticles, the endotoxins release BC causing an increase in the fluorescence intensity of BC. The change in fluorescence intensity of BC can be determined using a commercially available plate reader (Biotek). To determine the level of endotoxin removal by the polymeric nanoparticles, the background fluorescence intensities of BC and polymeric nanoparticle control (NPs), BC and endotoxin control, BC alone were subtracted to avoid any interferences. The endotoxin removal efficiency were determined by Eq. 1, which calculates the amount (%) of endotoxin removed by the polymeric nanoparticles based on the change in fluorescence intensity levels of the samples described above.

$$\% \text{ endotoxin removal} = 100 \times \div \frac{FI \text{ of}\left(\begin{array}{c}BC \text{ plus endotoxin plus } NPs - \\ BC \text{ plus endotoxin}\end{array}\right)}{FI \text{ of } (BC \text{ plus } NPs - BC \text{ alone})} \quad (\text{Eq. 1})$$

In certain aspects, the polymeric nanoparticles can have an endotoxin removal efficacy per unit surface area of the polymeric nanoparticle(s) of at least about $3 \times 10^5$ endotoxin units per cm$^2$ of the outer surface area of the polymeric nanoparticles (EU/cm$^2$), or at least about $1 \times 10^6$ EU/cm$^2$, or about $1.49 \times 10^6$ EU/cm$^2$. The endotoxin removal efficacy per unit surface area of the polymeric nanoparticle(s) can be calculated using the fluorescence displacement assay described above.

In calculating the endotoxin removal efficacy per unit outer surface area of the polymeric nanoparticle, the number of nanoparticles is first calculated according to Equation 2 below:

$$\text{Number of polymer nanoparticles per ml} = \frac{(6\ W \times 10^{12})}{\rho \times \pi \times \varphi^3} \quad (\text{Eq. 2})$$

where, W is the concentration of polymeric nanoparticles in g/ml, $\rho$ is the density of polymeric nanoparticles in g/ml, and $\varphi$ is the diameter of the polymeric particles in $\mu$m. It should be understood that these values can be determined by one skilled in the art using conventional techniques. For example, the diameter of the particles or the average diameter of the particles can be determined using transmission electron microscopy (TEM), and/or Dynamic Light Scattering (DLS). The number of endotoxin units (EU) per unit outer surface area of the polymeric nanoparticles can be calculated according to the following equation (3):

$$EU \text{ per unit outer surface area of polymeric nanoparticles} = \frac{\text{Total endotoxin removal by nanoparticles per ml of test solution}}{(\text{surface area of each nanoparticle}) \times (\text{number of polymeric nanoparticles per ml})} \quad (\text{Eq. 3})$$

In various aspects, the polymeric nanoparticles can have an endotoxin removal capacity of at least about $1.5 \times 10^7$ endotoxin units per gram of polymeric nanoparticle (EU/g), at least about $1 \times 10^8$ EU/g, at least about $1 \times 10^9$ EU/g, or at least about $7 \times 10^9$ EU/g, or about $7.9 \times 10^9$ EU/g. The endotoxin removal capacity can be determined by dividing total endotoxin removal by nanoparticles per ml of test solution by the nanoparticle concentration in g/mL.

In one or more aspects, the polymeric nanoparticles can be synthesized in any manner known to one skilled in the art. In certain aspects, the polymeric nanoparticles can be synthesized using a one-step phase separation technique. Generally, in such aspects, a solution of one or more polymers in an organic phase can be precipitated out into an aqueous phase.

In various aspects, the phase separation technique can include injecting a solution of one or more polymers in an organic solvent, such as toluene, into an aqueous solution. In certain aspects, the aqueous solution can include additives, such as surfactants, e.g., polyvinyl alcohol. It is appreciated that one skilled in the art understands that the concentration of polymer(s) in the organic solvent, the injection rate of the polymers into the aqueous solution, and/or the particular components of the aqueous solution can be modified to achieve specific sized and shaped nanoparticles.

In certain aspects, the concentration of polymer in the organic solvent can range from about 0.1 mg/mL to about 1000 mg/mL, or from about 1 mg/mL to about 100, or can be at least about 0.1 mg/mL, or at least about 1 mg/mL. In certain aspects, the concentration of polymer in the organic solvent can be about 10 mg/mL.

In one or more aspects, the flow rate or injection rate of the organic solvent comprising one or more polymers into the aqueous phase can range from about 0-1000 µL/sec.

Without being bound to any particular theory, when using the phase separation technique to make the polymeric nanoparticles, it is believed that the polymeric nanoparticles can be formed by phase separation at the boundary where the organic solvent slowly diffuses into the aqueous solution. Further, without being bound to any particular theory, it is believed that the polymeric nanoparticles can form by virtue of van der Waals attractive forces between the individual polymer molecules under low shear stress. Stated differently, without being bound by any particular theory, as polymer molecules start precipitating out of an organic phase into an aqueous phase, the molecules can accumulate and form spheres or other shapes under slow stirring conditions.

FIG. 1 depicts an exemplary system 100 that can be utilized to synthesize polymeric nanoparticles using a phase separation technique. The system 100 can include a syringe pump 102 for injecting one or more polymer-containing solutions into an aqueous solution 106 housed in a vessel 108. A homogenizer 110 can also be positioned inside the vessel 108. It is appreciated that the components of this system 100 are commercially available and well known to one skilled in the art.

In certain aspects, polymeric nanoparticles may be made by injecting an organic solvent having a predetermined concentration of polymer therein into an aqueous solution using a syringe pump, such as the syringe pump 102 of the system 100 of FIG. 1. In one aspect, the concentration of the polymer can be 10 mg/mL, the polymer can include PCL, and the organic solvent can include toluene. Further, in such an aspect, the aqueous solution can include about 1% w/v polyvinyl alcohol. To form the polymeric nanoparticles, the organic solvent and polymer solution can be delivered into the aqueous solution at a predetermined rate with constant stirring and/or homogenizing, e.g., using the homogenizer 110. In various aspects, the polymer dispersion may be homogenized using the homogenizer 110 at about 300 rpm for a predetermined period of time. The polymer dispersion may be stirred continuously for an extended period of time to remove any residual organic solvent by evaporation. After the residual organic solvent is removed by evaporation, the polymeric nanoparticles may then be separated from the aqueous phase by centrifugation, repeating this step as necessary with added water, for washing the polymeric nanoparticles from any residual organic solvents. Then, the polymeric nanoparticles may be lyophilized, weighed, and stored at a temperature of about 4° C.

As discussed above, in certain aspects, the polymeric nanoparticles can be utilized to remove endotoxins from various fluids, such as aqueous solutions. In various aspects, the versatility of the polymeric nanoparticles may be enhanced when the polymeric nanoparticles are associated with one or more types of support members, such as a film, membrane, or beads. In such aspects, the support member may enhance the binding of endotoxin to the polymeric nanoparticles through non-specific binding of the endotoxin to the support member material, which can increase the local concentration of the endotoxin allowing for increased binding to the polymeric nanoparticles. In the same or alternative aspects, the support member may provide an efficient endotoxin separation mechanism by immobilizing the polymeric nanoparticles so an endotoxin-free fluid or reduced-endotoxin fluid can flow through or past the immobilized polymeric nanoparticles bound with endotoxin.

An exemplary support member may include a film or membrane. Commercially available films or membranes are suitable for use with the polymeric nanoparticles, such as cellulose films, or various types of filter paper. In such aspects, the polymeric nanoparticles may be embedded in the film or membrane and/or can be affixed to at least one exterior surface of the film or membrane.

In one exemplary aspect, a cellulose based nanoparticle film can be prepared by: 1) preparing a 50:50 solution of ethanol and isobutanol; 2) preparing a 20% NaOH—deionized water solution; 3) weighing 20 g of alpha cellulose powder; 4) adding 200 ml ethanol-isobutanol solution; 5) mixing the cellulose mixture with stir bar at 900 rpm until well-mixed (approx. 10 minutes); 6) adding NaOH solution drop by drop until pH reaches 9.0; 7) setting the solution in oven until temperature is 60° C.; 8) setting the stir bar to 900 rpm for 30 minutes in oven; 9) adding sodium chloroacetic acid drop by drop until the pH reaches 7.0; 10) neutralizing and purify CMC solution with 20 ml of 96% ethanol; 11) adding polymeric nanoparticles; 12) pouring the liquid through 40 µm strainer onto an aluminum plate; 13) spread the liquid evenly on plate; and 14) let sit over-night. It is appreciated that one or more alterations can be made to such a nanoparticle film preparation.

Figure 2:
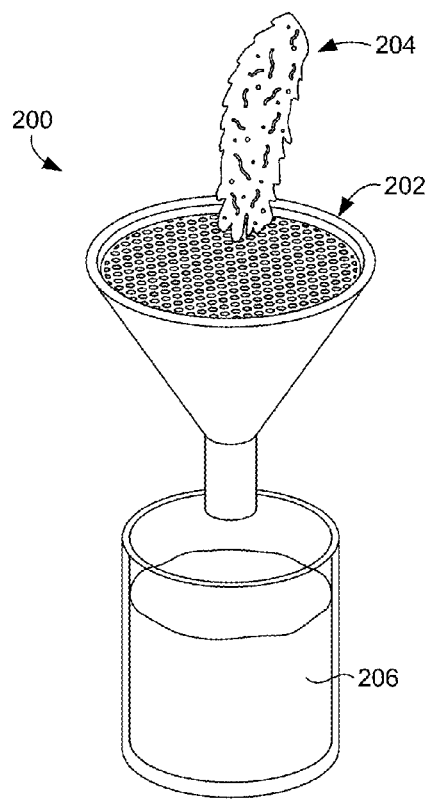
FIG. 2 is a schematic depiction of an endotoxin removal system, according to an aspect of the invention.

FIG. 2 depicts one exemplary filtering system 200 having a film or membrane 202 embedded with polymeric nanoparticles. FIG. 2 also depicts a fluid 204 containing endotoxin being exposed to the membrane 202. In the system 200, the polymeric nanoparticles can bind to the endotoxin present in the fluid 204. Since the polymeric nanoparticles are immobilized on the membrane 202, the remainder of the fluid can pass through the membrane 202 thereby forming an endotoxin-free or reduced endotoxin fluid 206.

In alternative aspects, the polymeric nanoparticles may be immobilized on the outer surface of beads, such as beads comprising silica, silicon, cellulose, or a mixture thereof. It is appreciated that one skilled in the art would understand how to immobilize the polymeric nanoparticles on the outer surface of the beads using conventional techniques. In one exemplary aspect, the polymeric nanoparticles maybe covalently attached via a functional group present in the polymer, e.g., an ester or amine group.

In various aspects, both the beads and the polymeric nanoparticles may be considered non-porous, such that an endotoxin-containing fluid does not enter the beads or polymeric nanoparticles in order to remove endotoxin from the fluid. This is unlike, for example, other various filtering techniques, where the endotoxin-containing fluid may enter pores or channels in a particle, and where the endotoxin gets trapped and an endotoxin free fluid flows out of the pores or channels resulting in an endotoxin-free fluid.

In certain aspects, beads having polymeric nanoparticles immobilized thereon may be loaded onto columns, cartridges, or corks to be used in line with, for example, an IV line, to remove any residual endotoxins in IV fluids that may be potentially harmful for patients.

Figure 3:
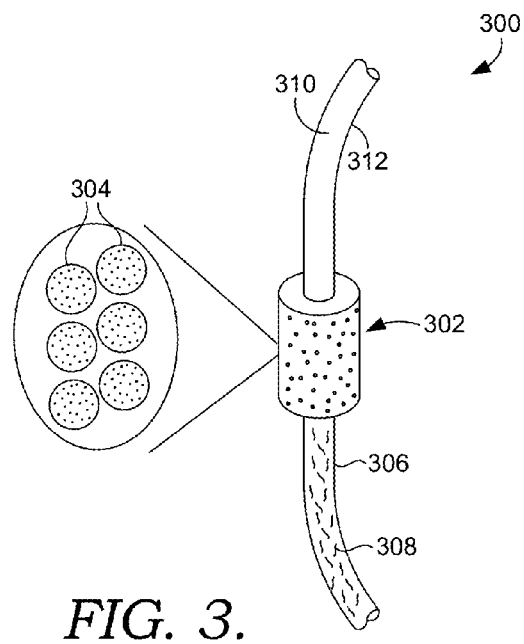
FIG. 3 is a schematic depiction of another endotoxin removal system, according to an aspect of the invention.

FIG. 3 depicts one exemplary filtering system 300 using an inline filtering device for endotoxin removal. The system 300 can include a filtering device 302 having beads 304 with polymeric nanoparticles immobilized on the outer surface of the beads 304. A fluid line 306 can include a fluid 308 having endotoxin therein. The filtering device 302 can be positioned in the path of the fluid flow such that the fluid 308 having endotoxin flows through the filtering device 302, allowing at least a portion of the endotoxin to bind to the polymeric nanoparticles present on the surface of the beads 304, thereby allowing a endotoxin-free or reduced endotoxin fluid 310 to flow through the line 312 exiting the filtering device 302.

In an embodiment not depicted in the figures, the polymeric nanoparticles may be immobilized on the inner surface of a fluid line so that as a fluid flows, the polymeric nanoparticles can bind to endotoxin and thereby form an endotoxin-free of reduced endotoxin fluid.

From the foregoing, it will be seen that this invention is one well adapted to attain all the ends and objects hereinabove set forth together with other advantages which are inherent to the systems and methods.

It will be understood that certain features and subcombinations are of utility and may be employed without reference to other features and subcombinations. This is contemplated by and is within the scope of the claims.

Since many possible aspects may be made of the invention without departing from the scope thereof, it is to be understood that all matter herein set forth or shown in the accompanying drawings is to be interpreted as illustrative and not in a limiting sense.

EXAMPLES

The concepts discussed herein will be further described in the following examples, which do not limit the scope of the various aspects described in the claims.

Each experiment in the below examples that included quantified measurements was carried out in at least three independent experiments with triplicate measurements. Data were summarized using means and standard deviations.

Example 1

Synthesis of PCL Nanoparticles

In this example, PCL nanoparticles were prepared by a phase separation method. A 10 mg/mL PCL (Sigma) solution in toluene was injected into a 1% w/v polyvinyl alcohol (PVA) surfactant aqueous solution using a syringe pump (kD Scientific). The mixture was homogenized at 300 rpm. The dispersion was stirred overnight at room temperature (~22° C.) to remove residual toluene. The polymeric nanoparticles were separated from the dispersion by centrifugation at 4,600 rcf for 20 min. Particles were washed by centrifugation three times using deionized water. The resulting nanoparticles were lyophilized, weighed and stored at 4° C. until further use.

Example 2

Characterization of PCL Nanoparticles—Shape, Size, and Surface Charge

Figure 4:
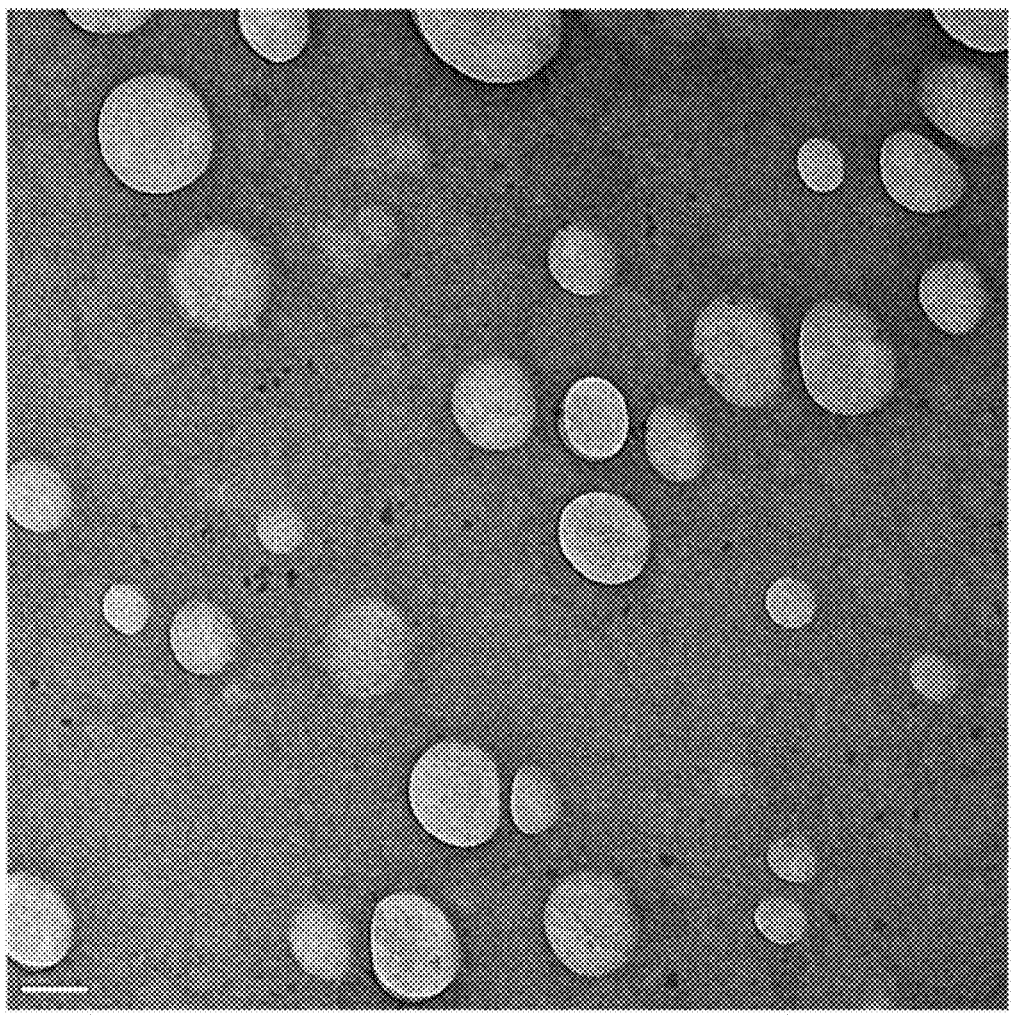
FIG. 4 is a transmission electron microscopy image of a sample of polymeric nanoparticles as described in Example 2, according to an aspect of the invention.

The shape and size of the polymeric PCL nanoparticles prepared in Example 1 were analyzed by TEM (Tecnai F20) at 120 kV. FIG. 4 shows a TEM image of a sample of the polymeric nanoparticles prepared as in Example 1. As seen in the TEM image in FIG. 4, the polymeric nanoparticles are substantially uniform in size and are approximately spherical. The polymeric PCL nanoparticles prepared as in Example 1 provided nanoparticles having a maximum dimension or maximum diameter of 398.3±95.13 nm in large quantities.

Figure 5A:
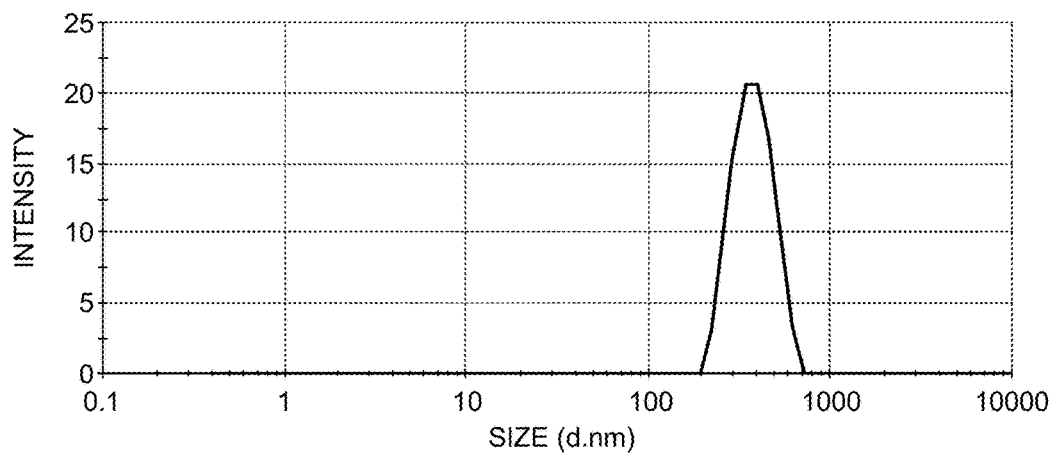
FIG. 5A is a graph of the size distribution by intensity for a sample of polymeric nanoparticles as measured by dynamic light scattering as described in Example 2, according to an aspect of the invention.

The size distribution and surface charge of the polymeric PCL nanoparticles in water were measured by dynamic light scattering (DLS; Malvern NanoSeries Zetasizer ZS90). Polymeric nanoparticle suspensions were prepared in 0.2 µm syringe filtered deionized water in concentrations of 0, 10, 100 and 1000 µg/ml. The suspensions were vigorously stirred for a minute and sonicated (Branson). DLS measurements were performed at 25° C. in disposable capillary cells (Malvern) using the backscattering detection at 90°. The size distribution was obtained for 100 successive runs. The zeta potential was measured for 15 runs. Data was analyzed using means and standard deviations of the three concentrations. FIG. 5A shows a graph of the size distribution of the polymeric nanoparticles by intensity. As seen in FIG. 5A, there is a single peak that is consistent with an approximate diameter of about 300 nm to about 500 nm for the polymeric nanoparticles produced as in Example 1, and which confirms the size distribution measured using TEM. The size distribution was further confirmed by DLS with a polydispersity index of 0.2. The uniform size, as determined by both DLS and TEM, confirm that the polymeric nanoparticles did not aggregate after drying and dispersing in suspension when forming the nanoparticles as described in Example 1.

Figure 5B:
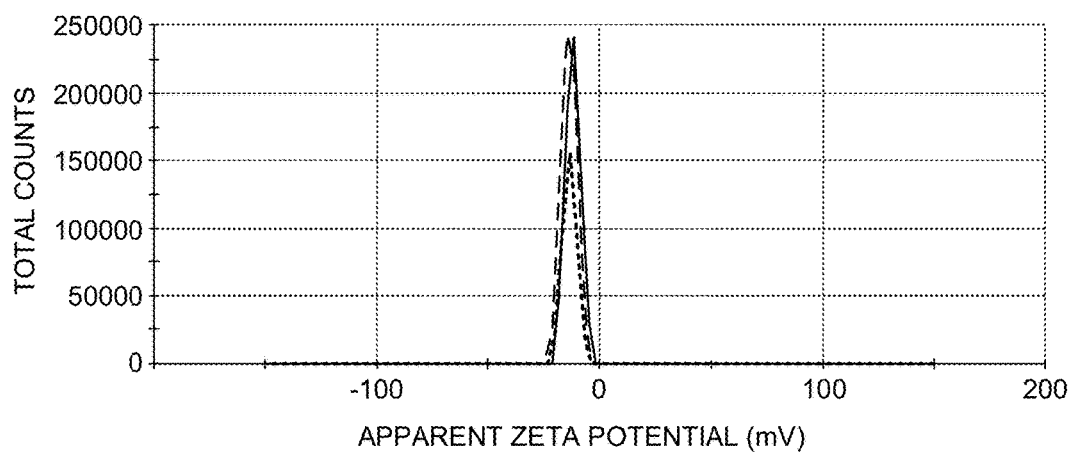
FIG. 5B is a graph of the zeta potential distribution for a sample of polymeric nanoparticles as measured by dynamic light scattering as described in Example 2, according to an aspect of the invention.

FIG. 5B shows the zeta potential distribution, which shows that the polymeric PCL nanoparticles produced as in Example 1 are slightly negative at −12.4±8.28 mV.

Example 3

Quantification of Endotoxin Removal by the Polymeric Nanoparticles

A polymeric nanoparticle BODIPY-Cadaverine (BC)-based fluorescence assay was employed in order to determine the endotoxin binding efficacy. *E. coli* 055:B5 endotoxin (Sigma) from *E. coli* bacteria was used as an exemplary endotoxin in this assay.

First, an optimum mass ratio of BC and endotoxin was determined. BC (Invitrogen) was dissolved in dimethyl sulfoxide (DMSO; Sigma) to prepare a stock concentration of 3.33 mg/ml. The excitation and emission wavelengths for BC were 485/20 and 528/20 nm, respectively. The molar ratio of BC and endotoxin was determined from quenching of BC fluorescence intensity (F.I.) using a plate reader (Biotek Synergy). BC of 262.11 µg/ml was added to different concentrations of endotoxin from 0-50 µg/ml in DI water of pH~7.4 at 25° C. in a 96-well plate (Corning).

Figure 6:
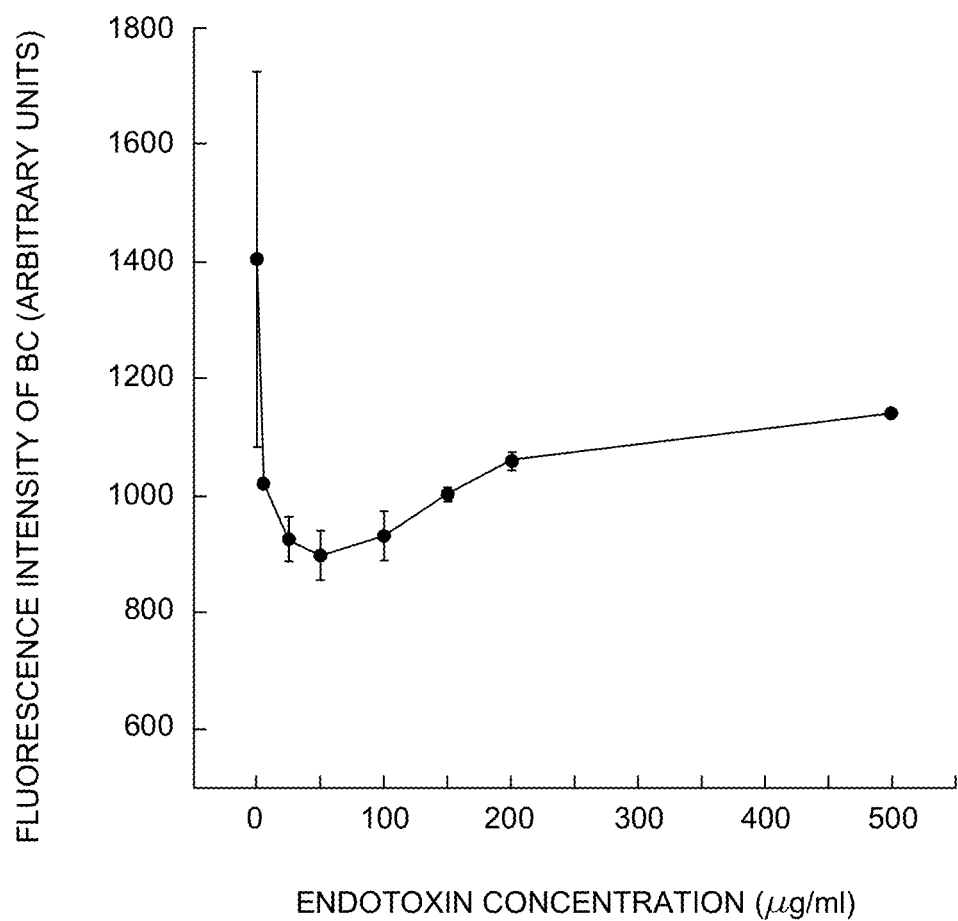
FIG. 6 is a graph of the florescence intensity of BODIPY-Cadaverine (BC) as a function of endotoxin concentration as described in Example 3, according to an aspect of the invention.

FIG. 6 shows a plot of the fluorescence intensity of BC at 262.11 µg/mL versus various endotoxin concentrations. In the absence of endotoxins, BC exhibited the highest fluorescence intensity (1405.2±322.2). The addition of endotoxin to BC sharply decreased the fluorescence intensity of BC, indicating fast binding and rapid saturation of BC with endotoxin via quenching mechanisms. Addition of more endotoxin beyond 50 µg/ml endotoxin increased the fluorescence intensity of BC indicating that there was an optimum BC:endotoxin working ratio of 5.24 w:w ratio. 50 µg/ml endotoxin were used to evaluate the binding efficiency of the polymeric nanoparticles.

Figure 7:
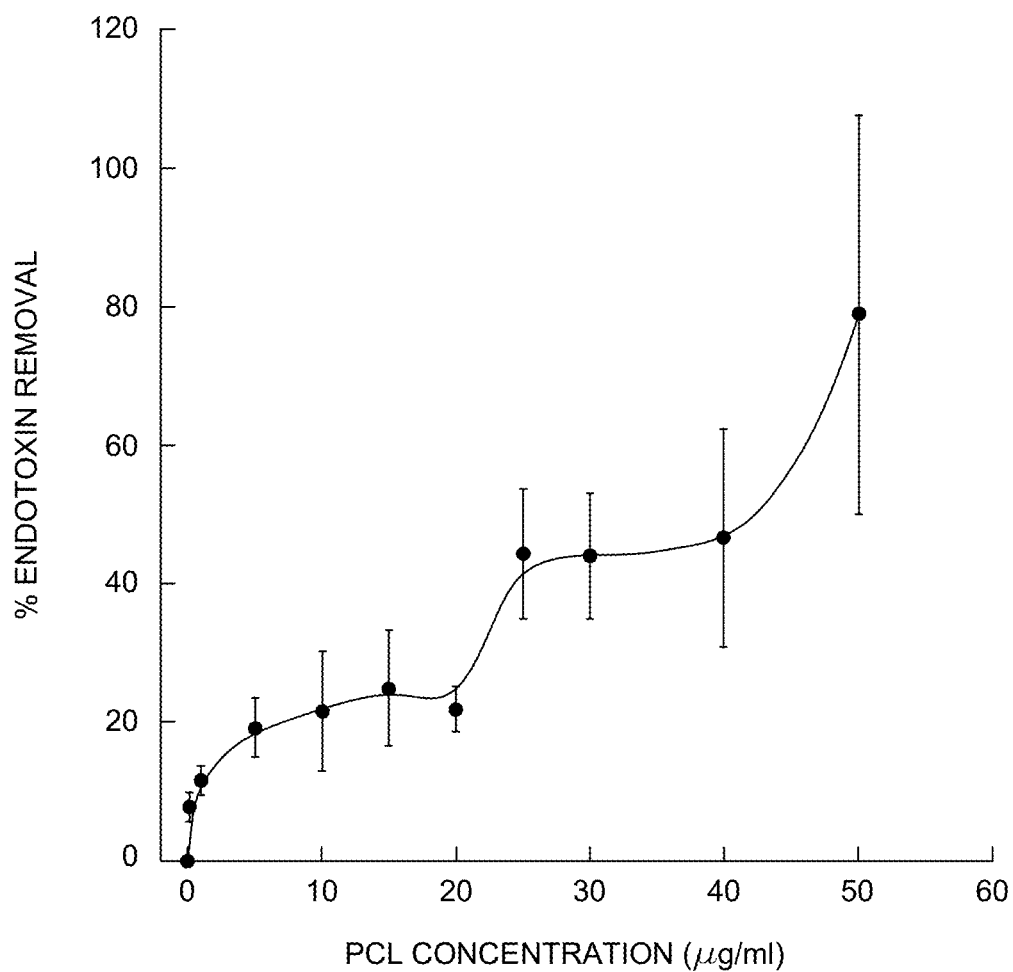
FIG. 7 is a graph showing the percent endotoxin removal as a function of the concentration of polymeric nanoparticles as described in Example 3, according to an aspect of the invention.

Using this BC:endotoxin working ratio, the quantification of endotoxin removal via the polymeric nanoparticles was determined. As mentioned above, the binding of endotoxin was determined using a BC fluorescence displacement assay. In this displacement assay, 50 µg/ml endotoxin was mixed with 262.11 µg/ml BC in 0.6 ml deionized water (pH~7.4) in a 1.5 ml centrifuge tube (Corning). Serial dilutions of polymeric PCL nanoparticles (made as above) of 0, 0.1, 1, 2, 5, 10, 15, 20, 25, 30, 40 and 50 µg/ml were added to the tube to measure endotoxin-binding efficiency. As endotoxins became bound to the surfaces of the polymeric PCL nanoparticles, the endotoxins released BC causing an increase in BC fluorescence intensity. The change in fluorescence intensity of BC was determined using the plate reader (Biotek). The background fluorescence intensities of BC and polymeric nanoparticle control, BC and endotoxin control, BC alone were subtracted to avoid any interferences. The % endotoxin removal efficiency of the various concentrations of polymeric PCL nanoparticles were determined by Eq. 1 listed above. FIG. 7 shows a plot of the percent endotoxin removal efficiency against the various polymeric PCL concentrations.

When the polymeric nanoparticles were added to the aqueous mixture of BC and endotoxin (5.24 w:w ratio), the polymeric nanoparticles competitively bound to endotoxin displacing its binding with BC. As a result and as can be seen in FIG. 7, the fluorescence intensity of BC increased from its quenched state in equilibrium with endotoxin with the endotoxin binding to the polymeric nanoparticles. As binding increased between endotoxin and the polymeric nanoparticles, the % increase in fluorescence intensity of BC also increased, indicating a proportional relationship between the two. The % increase in fluorescence intensity of BC was used to calculate endotoxin-binding removal efficiencies of polymeric PCL nanoparticles by Eq. 1. PCL nanoparticles effectively removed up to 78.78±28.84% endotoxin.

The binding curve of FIG. 7 showed a two-step mechanism reflecting the formation of initial endotoxin hitchhiking at low concentrations to multiple endotoxin hitchhiking to a single nanoparticle as the concentration reaches to saturation. Indeed, as described in Example 5 below, TEM images (in FIGS. 8A and 8B) show multiple endotoxin molecules binding to the same polymeric nanoparticle.

Example 4

Comparison of Endotoxin Removal Efficacy Per Unit Surface Area

The efficiency of endotoxin removal per unit outer surface area of the polymeric nanoparticles was calculated, and compared with that reported for a commercially available membrane (Pall). The calculations were done using Eq. 2 as described above, where, W is the concentration of nanoparticles in g/ml, $\rho$ is the density of PCL polymer in g/ml, and $\varphi$ is the diameter of the PCL nanoparticles in µm. In the present example, the number of polymeric PCL nanoparticles/ml was calculated for 50 µg/ml, which showed the highest endotoxin removal efficacy with a $\rho$ of 1.146 g/ml at 25° C. and a particle diameter of $\varphi$=0.398 µm. Then the total number of polymeric PCL nanoparticles and the total outer surface area of polymeric PCL nanoparticles in the final volume of 0.6 ml were calculated. These values appear in Table 1, below.

TABLE 1

Endotoxin and nanoparticle values

| PCL nanoparticle concentration, W (g/ml) | PCL nanoparticle density, $\rho$ (g/ml) | Diameter of a PCL nanoparticle, $\varphi$ (µm) | PCL nanoparticles/ml by Eq. (2) | Surface area/ nanoparticle (cm$^2$/ml) | Endotoxin concentration (EU/ml) | Endotoxin removal (EU/cm$^2$ nanoparticle) |
|---|---|---|---|---|---|---|
| $5 \times 10^{-5}$ | 1.146 | 0.3983 | $2.1 \times 10^8$ | 0.335 | $5 \times 10^5$ | $1.49 \times 10^6$ |

Finally, the number of EU per unit area of nanoparticles was calculated by equation 3 described above. The total endotoxin removal per unit outer surface area of polymeric nanoparticle was $1.49 \times 10^6$ EU/cm$^2$.

The removal efficacy per unit outer surface area of the polymeric nanoparticles ($1.49 \times 10^6$ EU/cm$^2$) is 6.7 fold more efficient than a commercially available hydrophobic charged microporous membrane. A membrane that has a porous hydrophobic polyether sulfone matrix, and polyamines within the matrix (Pall Corporation) has been shown to bind up to $2.23 \times 10^5$ EU/cm$^2$. Porous silica gel matrix with silica particles showed endotoxin removal capacity of $1.2 \times 10^7$ EU/g, while PCL nanoparticles removed almost 655 times more ($7.9 \times 10^9$ EU/g) endotoxin with an initial concentration of $0.5 \times 10^6$ EU/ml. Cellulose beads in an ETClean chromatographic column have been shown to provide a removal capacity of $4.8 \times 10^6$ EU/ml. These results suggest that a support based system could be utilized, such as embedding the polymeric nanoparticles or affixing the polymeric nanoparticles to a support member as discussed above, to further enhance the endotoxin removal capacity of the polymeric nanoparticles.

Example 5

Figure 8A:
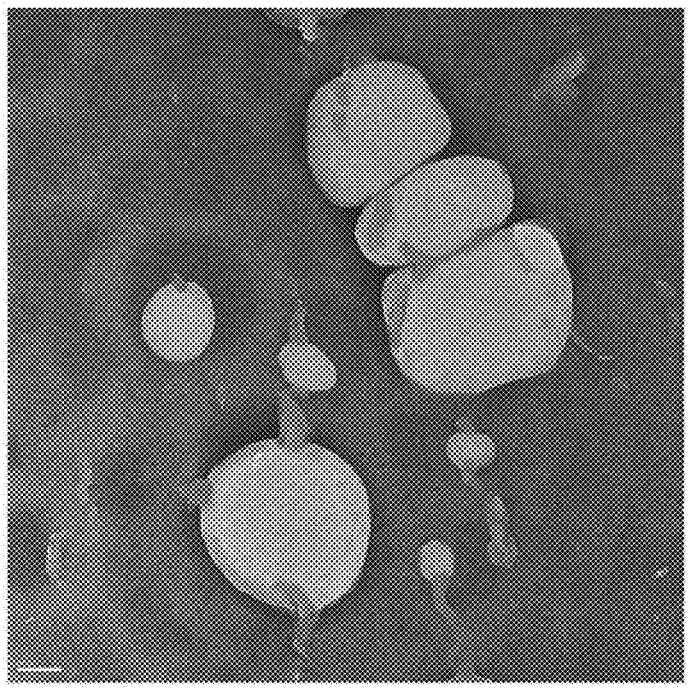
FIGS. 8A and 8B are transmission electron microscopy images showing endotoxins bound to the polymeric nanoparticles as described in Example 5, according to an aspect of the invention.
Figure 8B:
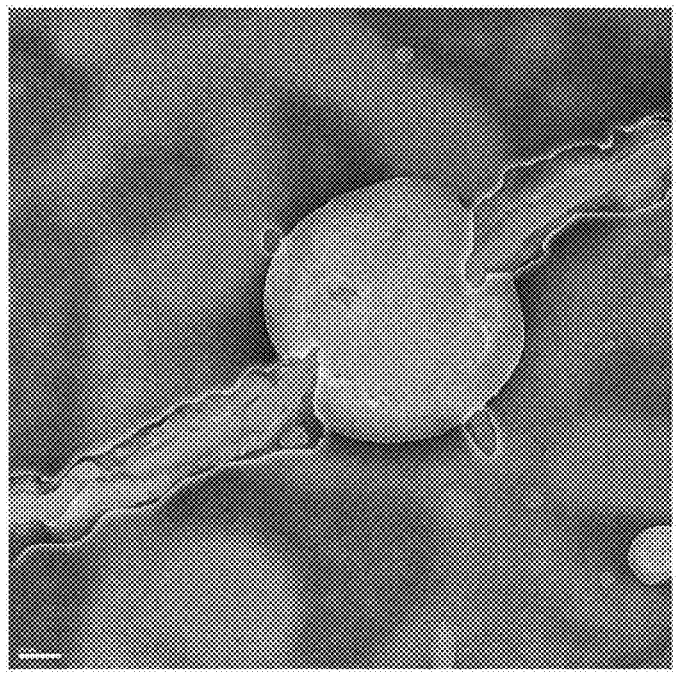

Endotoxin-PCL Nanoparticle Binding as Imaged by TEM and Measured by Surface Charges TEM was used for high-magnification visualization of endotoxin binding on polymeric PCL nanoparticles. 50 µg/ml endotoxin was incubated with 50 µg/ml polymeric PCL nanoparticles produced as in Example 1 in a 1.5 ml centrifuge tube for 10 min. 10 µl of the sample was put on top of a pre-wetted copper-carbon TEM grid (Tedpella), air-dried for an hour and further dried in a desiccator until being imaged by a TEM (Tecnai F20) at 120 kV. FIGS. 8A and 8B are two TEM images showing how more than one endotoxin molecule binds a single polymeric PCL nanoparticle.

Figure 9A:
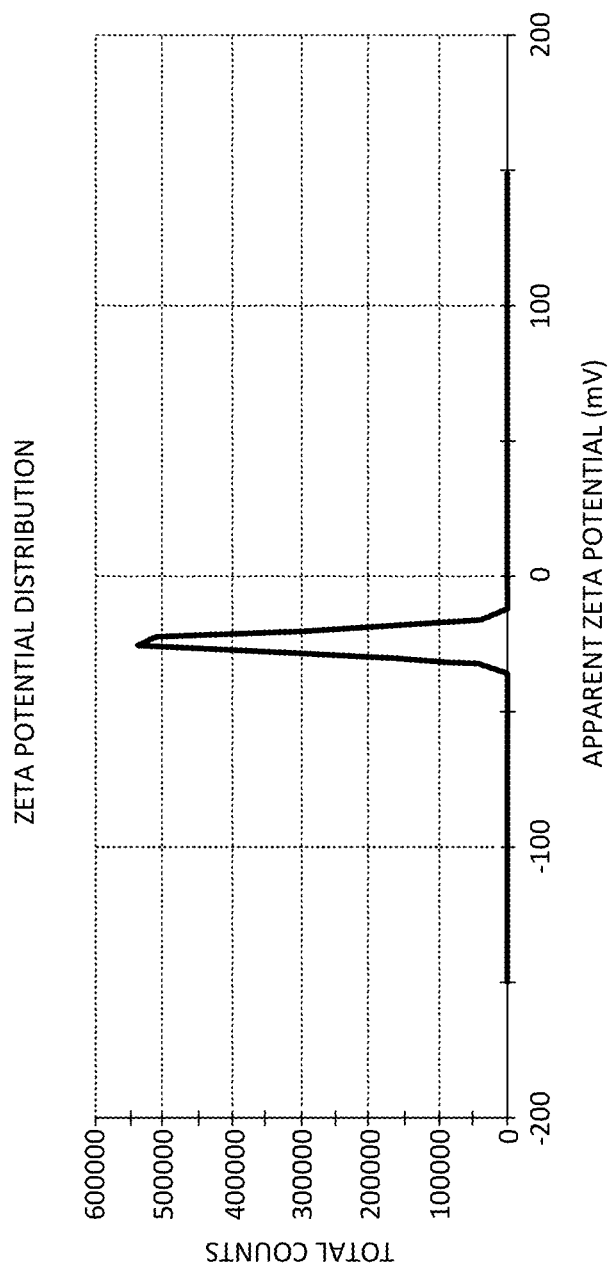
FIG. 9A is graph of a zeta potential distribution measurement for an endotoxin sample as described in Example 5, according to an aspect of the invention.
Figure 9B:
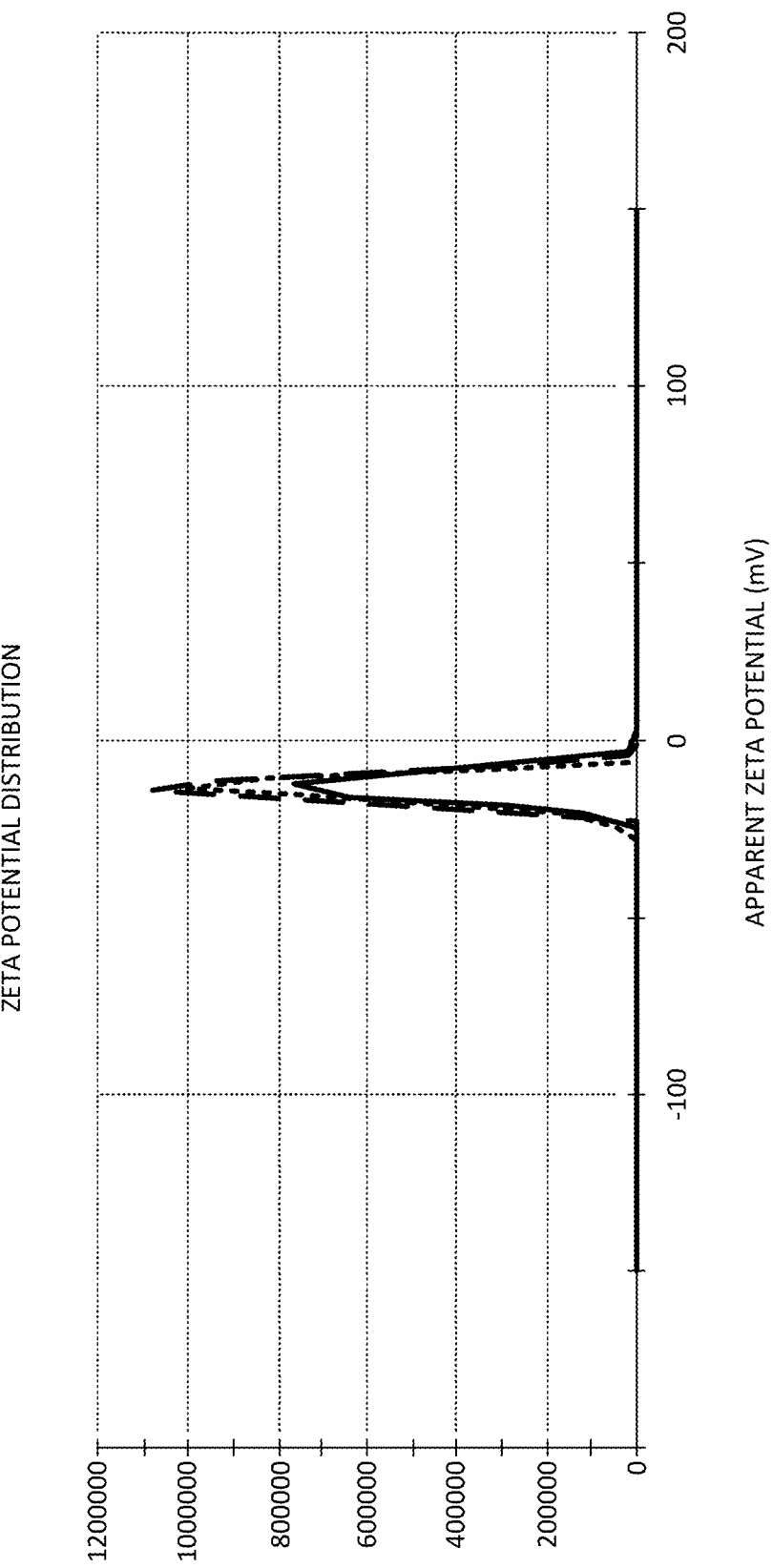
FIG. 9B is a graph of a zeta potential distribution measurement for the endotoxin sample in FIG. 9A compared to a zeta potential distribution measurement for the endotoxin sample after binding to a predetermined concentration of polymeric nanoparticles as described in Example 5, according to an aspect of the invention.

Endotoxin binding was also confirmed by changes in surface charges of endotoxin solution alone and endotoxin-PCL mixture. Samples were loaded in pre-rinsed folded capillary cells (Malvern) for surface charge measurements using a Nanoseries Zetasizer (Malvern). A minimum of three individual samples was measured. FIG. 9A shows the zeta potential distribution of pure endotoxin, which exhibits a highly negative surface charge of −27.7±6.1 mV that was compensated by the net negative charge of PCL nanoparticles. After being hitchhiked on (or bound to) the nanoparticles, the net surface charge of endotoxins increased to −14.7±3.63 mV (as seen in FIG. 9B), indicating a charge overcompensation by polymeric PCL nanoparticle binding.

Example 6

Comparison of Endotoxin Binding to Nanoparticles and Polymers

Figure 10A:
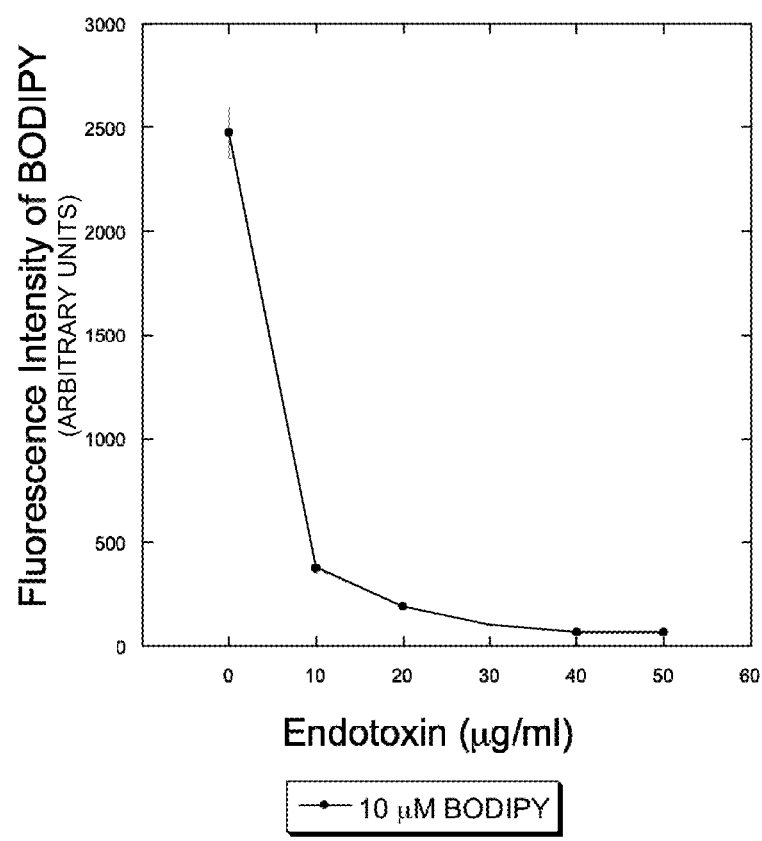
FIG. 10A is a graph showing the fluorescence intensity of BODIPY as a function of endotoxin concentration, according to an aspect of the invention.
Figure 10B:
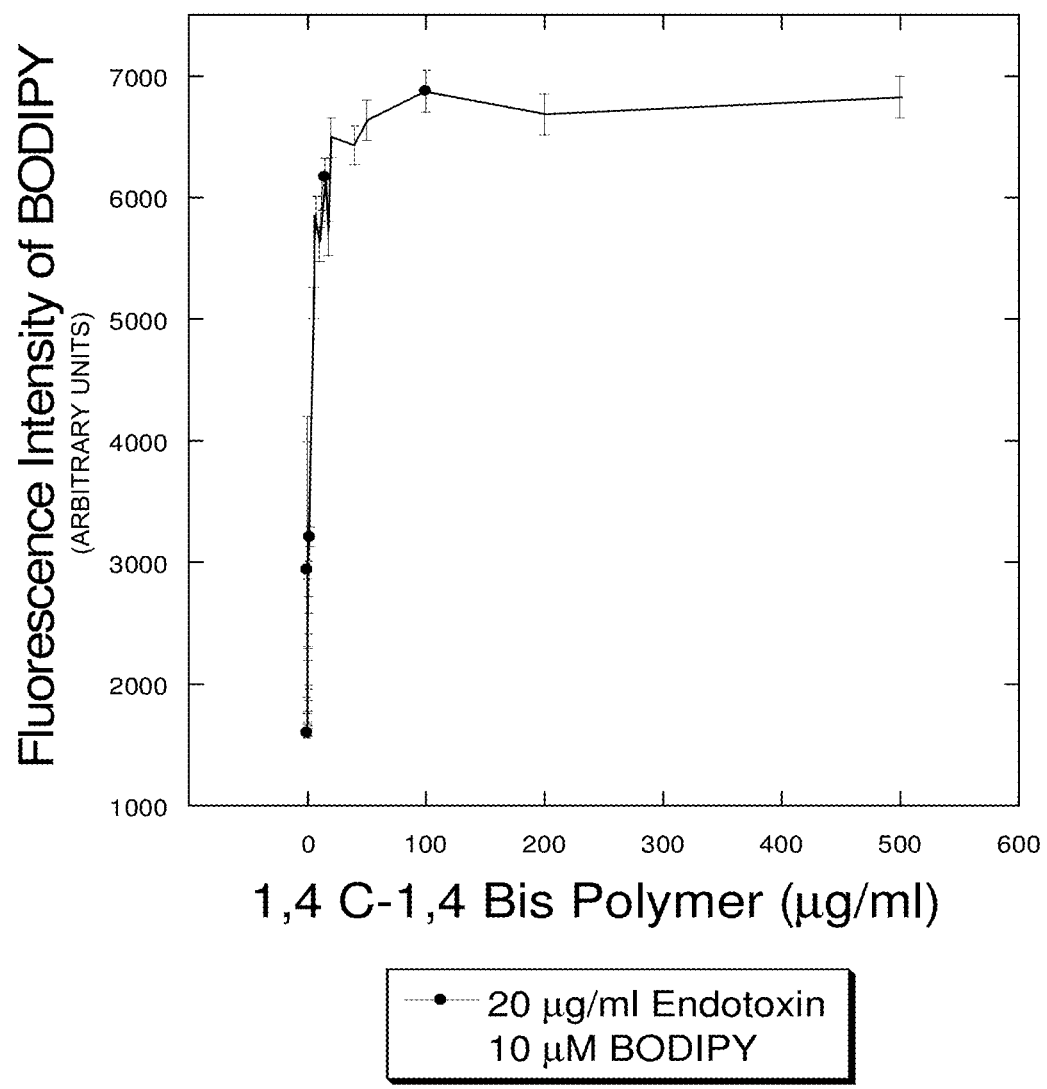
FIG. 10B is a graph showing the fluorescence intensity of BODIPY as a function of 1,4 C-1,4 bis polymer concentration, according to an aspect of the invention.
Figure 10C:
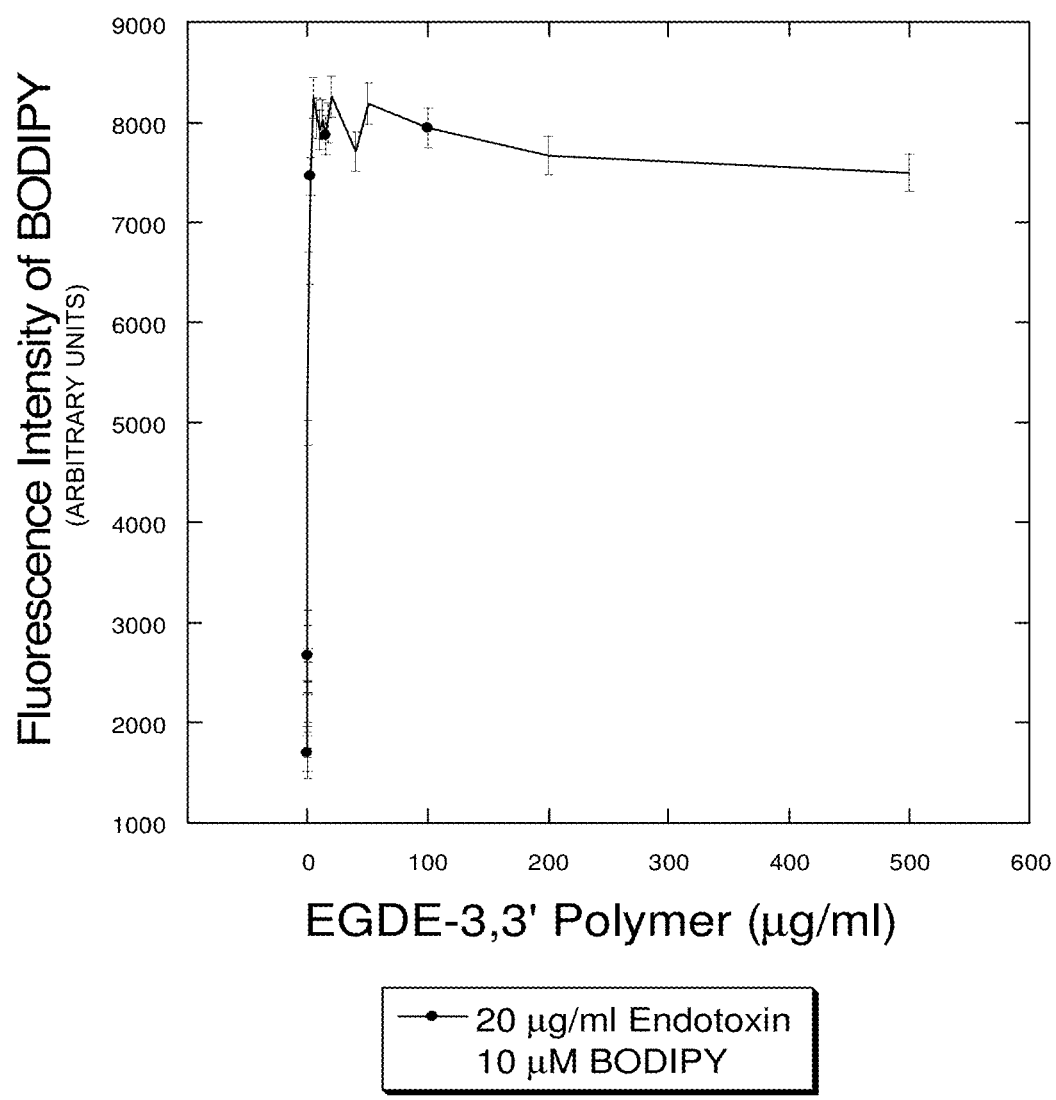
FIG. 10C is a graph showing the fluorescence intensity of BODIPY as a function of EGDE-3,3' polymer concentration, according to an aspect of the invention.
Figure 10D:
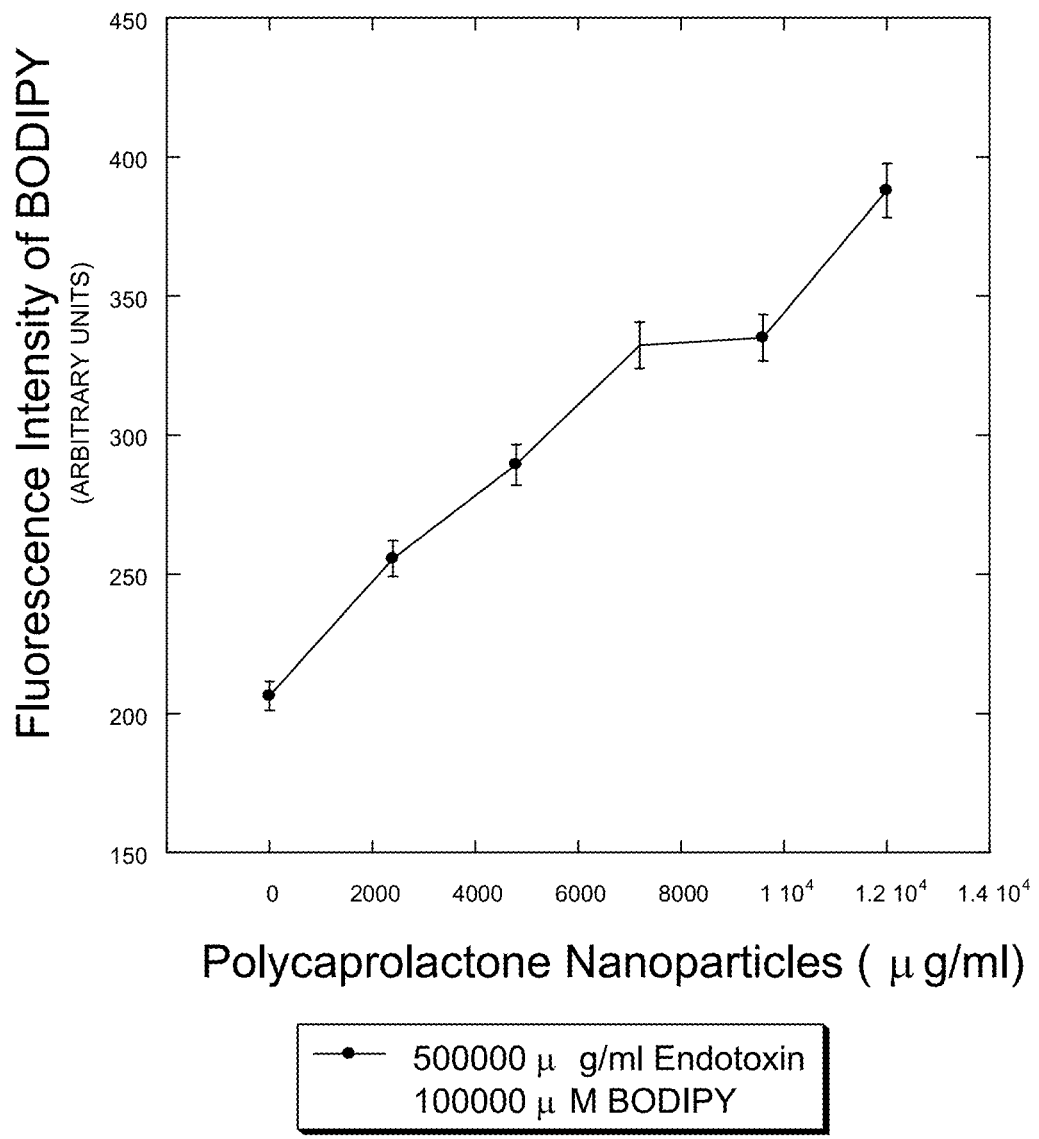
FIG. 10D is a graph showing the fluorescence intensity of BODIPY as a function of PCL nanoparticle concentration, according to an aspect of the invention.
Figure 10E:
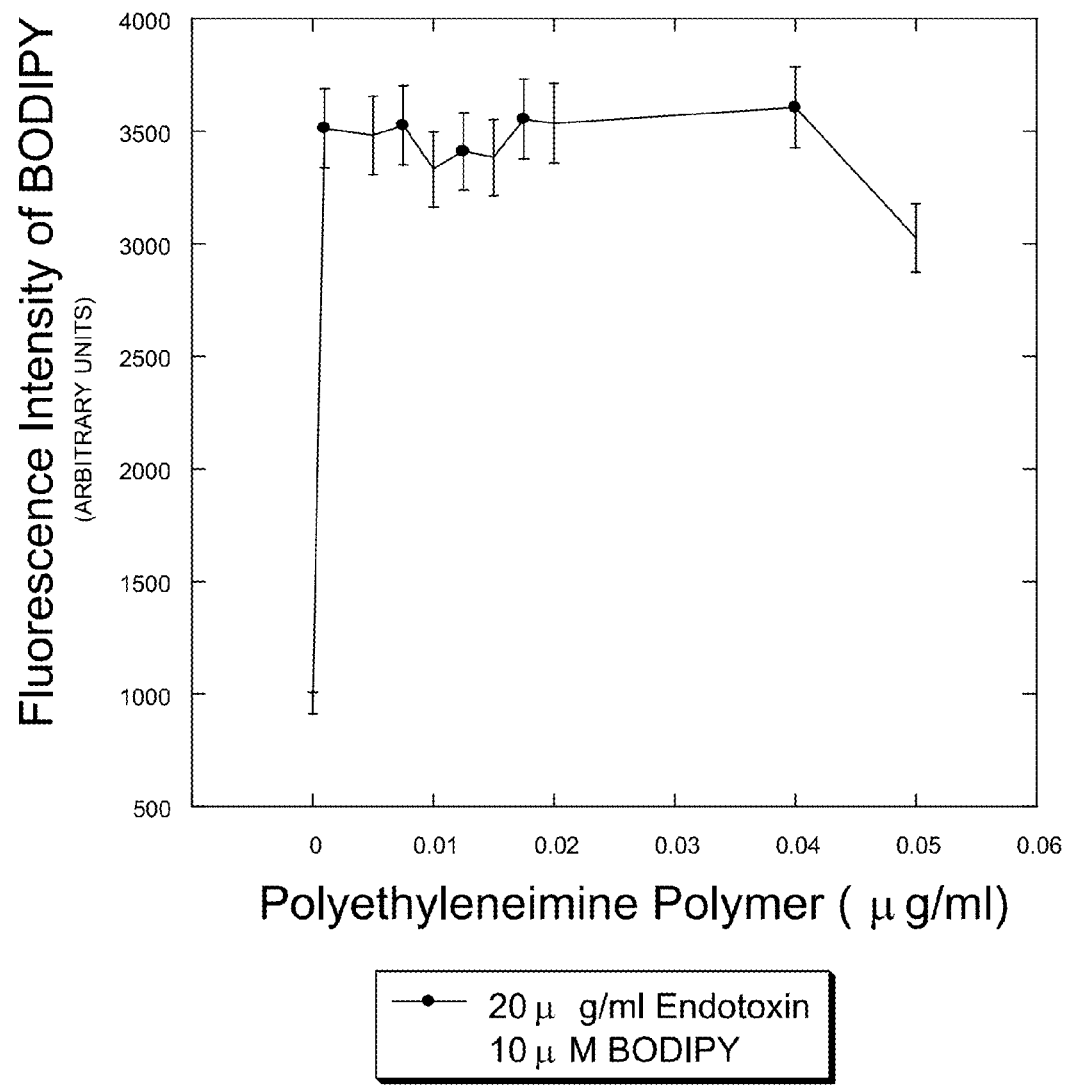
FIG. 10E is a graph showing the fluorescence intensity of BODIPY as a function of polyethyleneimine polymer concentration, according to an aspect of the invention.

A fluorescence-based assay was utilized to compare the endotoxin binding ability of PCL nanoparticles to various polymers. As can be seen in FIG. 10A, the fluorescence intensity of BODIPY decreases with increasing amounts of endotoxin (e.g., $E.\ coli$ 055:B5 endotoxin). It is believed that the endotoxin binds to BODIPY and quenches the BODIPY fluorescence signal. When the polymer or nanoparticles bind to the endotoxin, the endotoxin is no longer free to bind to BODIPY and quench the BODIPY fluorescence signal, thus the level of the BODIPY fluorescence signal correlates with the amount of polymer (or nanoparticle) binding to endotoxin (in the presence of BODIPY). FIGS. 10B-10E depicts the fluorescence intensity of BODIPY in the presence of varying concentration of various polymers (FIGS. 10B, 10C, and 10E) or in the presence of varying concentrations of PCL nanoparticles (FIG. 10D). Further, Table 2 below shows the maximum percent removal of endotoxin for the various polymers of nanoparticles, which was calculated based on the data in FIGS. 10A-10E.

TABLE 2

Comparison of Endotoxin Removal

| Polymer or Nanoparticle | Maximum Percent Removal of Endotoxin |
| --- | --- |
| 1,4 C-1,4 Bis Polymer | 72% |
| EGDE-3,3' Polymer | 77% |
| PCL nanoparticles | 47% |
| Polyethyleneimine Polymer | 73% |

As can be seen in FIGS. 10B-10E and Table 2, the polymers show endotoxin binding at lower polymer concentrations (compared to the PCL nanoparticle concentrations for endotoxin binding). However, as can be seen in FIG. 10D, the PCL nanoparticles can remove a high concentration of endotoxin.

Material cost analysis shows that polymeric nanoparticles, e.g., PCL nanoparticles, offer a significantly greater cost effectiveness. Table 3 shows a comparison of the costs associated with endotoxin removal by PCL nanoparticles versus a commercially available resin.

TABLE 3

Cost and Capacity Comparison of PCL Nanoparticles and a Commercial Resin

| Method | Price of Solution | Endotoxin Removal (ng/ml) |
| --- | --- | --- |
| Polycaprolactone Nanoparticles | $0.972/ml of solution | 2.50E+08 |
| Thermo Scientific Endotoxin Removal Resin | $27.20/ml of solution | 2.00E+05 |

As can be seen in Table 3, the PCL nanoparticles can remove at least $10^3$ more endotoxin per mL of nanoparticles compared to a mL of commercially available endotoxin removal resin.

What is claimed is:

1. An endotoxin removal system, comprising:
   a plurality of polymeric nanoparticles, each polymeric nanoparticle of the plurality of polymeric nanoparticles having a maximum dimension between 300 nm and 500 nm; and
   a support member associated with the plurality of polymeric nanoparticles, wherein, when an aqueous solution comprising endotoxin molecules is exposed to the endotoxin removal system, the support member and the plurality of polymeric nanoparticles are cooperatively configured to separate at least a portion of the endotoxin molecules from the aqueous solution, and wherein each polymeric nanoparticle of the plurality of polymeric nanoparticles has an endotoxin removal capacity of at least $1\times10^9$ endotoxin units per gram of polymeric nanoparticle (EU/g).

2. The endotoxin removal system of claim 1, wherein each polymeric nanoparticle of the plurality of polymeric nanoparticles has an endotoxin removal efficacy of at least $1\times10^6$ endotoxin units per $cm^2$ of polymeric nanoparticle surface area ($EU/cm^2$).

3. The endotoxin removal system of claim 1, wherein each polymeric nanoparticle of the plurality of polymeric nanoparticles comprises a polyester.

4. The endotoxin removal system of claim 3, wherein the polyester comprises Poly(ε-caprolactone) (PCL).

5. The endotoxin removal system of claim 1, wherein the support member comprises a film.

6. The endotoxin removal system of claim 5, wherein the film comprises cellulose.

7. The endotoxin removal system of claim 1, wherein the support member comprises a plurality of beads, the plurality of beads comprising silica, silicon, cellulose, or a mixture thereof.

8. A method for removing endotoxins from an aqueous solution, the method comprising:
   exposing an aqueous solution comprising endotoxin molecules to polymeric nanoparticles so that at least a portion of the endotoxin molecules bind to an exterior surface of one or more of the polymeric nanoparticles to form endotoxin-bound polymeric nanoparticles, wherein each of the polymeric nanoparticles has a maximum dimension of about 300 nm to about 500 nm, and wherein each of the polymeric nanoparticles have an endotoxin removal capacity of at least $1\times10^9$ endotoxin units per gram of polymeric nanoparticle (EU/g); and
   removing at least a portion of the aqueous solution from the endotoxin-bound polymeric nanoparticles.

9. The method of claim 8, wherein the polymeric nanoparticles comprise a polyester.

10. The method of claim 9, wherein the polyester comprises Poly(ε-caprolactone) (PCL), polylactic acid (PLA), Poly(lactic-co-glycolic acid (PLGA), hyaluronic acid (HA), poly(acrylic acid) (PAA), poloxamers, polyethylene oxide (PEO), polyethylene glycol (PEG), polyflutamic acid, or a mixture thereof.

11. The method of claim 8, wherein the polymeric nanoparticles are associated with a support member, wherein the support member comprises one of a film or a plurality of beads.

12. The method of claim 11, wherein the support member comprises the plurality of beads, wherein the plurality of beads comprise at least one of silica, silicon, or cellulose.

13. The method of claim 8, wherein each of the polymeric nanoparticles has an endotoxin removal efficacy of at least $1 \times 10^6$ endotoxin units per cm$^2$ of nanoparticle surface area (EU/cm$^2$).

14. The method of claim 8, wherein the removing at least a portion of the aqueous solution from the endotoxin-bound polymeric nanoparticles comprises flowing the at least a portion of the aqueous solution past the polymeric nanoparticles when the polymeric nanoparticles are at least partly immobilized by association with at least one of a film, a membrane, or beads.

15. A method for removing endotoxins from an aqueous solution, the method comprising:

exposing an aqueous solution comprising endotoxin molecules to polymeric nanoparticles so that at least a portion of the endotoxin molecules bind to an outer surface of one or more of the polymeric nanoparticles to form endotoxin-bound polymeric nanoparticles, wherein at least the outer surface of each of the polymeric nanoparticles comprises Poly(ε-caprolactone) (PCL), wherein each of the polymeric nanoparticles has a maximum dimension of about 300 nm to about 500 nm, and wherein the polymeric nanoparticles have an endotoxin removal capacity of at least about $1 \times 10^9$ endotoxin units per gram of polymeric nanoparticle (EU/g) and an endotoxin removal efficacy of at least $1 \times 10^6$ endotoxin units per cm$^2$ of nanoparticle surface area (EU/cm$^2$).

16. The method of claim 15, wherein the endotoxin molecules comprise an endotoxin from one or more Gram negative bacterial species.

17. The method of claim 16, wherein the one or more Gram negative bacterial species comprises *E. coli*.

18. The method of claim 15, wherein the polymeric nanoparticles are embedded in a film.

19. The method of claim 15, wherein the polymeric nanoparticles are coupled to beads.

20. The method of claim 15, wherein at least a portion of the polymeric nanoparticles are spherical.

* * * * *